(12) United States Patent
Yellin et al.

(10) Patent No.: US 11,857,418 B2
(45) Date of Patent: Jan. 2, 2024

(54) ANNULI ENGAGEMENT AND RESHAPING USING NATURAL FIDUCIALS

(71) Applicant: VALCARE, INC., Herzelyia Pituach (IL)

(72) Inventors: Nadav Yellin, Even Yehuda (IL); David Meerkin, Jerusalem (IL); Yoav Rozen, Binyamina (IL); Shuki Porath, Haifa (IL); Aviad Galler, Tel Aviv (IL); Yuri Falkovich, Pardes Hana (IL); Guy Rogel, Haifa (IL)

(73) Assignee: VALCARE, INC., Herzelyia Pituach (IL)

( * ) Notice: Subject to any disclaimer, the term of this patent is extended or adjusted under 35 U.S.C. 154(b) by 0 days.

(21) Appl. No.: 18/245,298

(22) PCT Filed: Sep. 15, 2021

(86) PCT No.: PCT/US2021/071468
§ 371 (c)(1),
(2) Date: Mar. 14, 2023

(87) PCT Pub. No.: WO2022/061345
PCT Pub. Date: Mar. 24, 2022

(65) Prior Publication Data
US 2023/0285148 A1    Sep. 14, 2023

Related U.S. Application Data

(60) Provisional application No. 63/078,759, filed on Sep. 15, 2020.

(51) Int. Cl.
A61F 2/24      (2006.01)
A61F 2/00      (2006.01)

(52) U.S. Cl.
CPC .......... *A61F 2/2466* (2013.01); *A61F 2/2448* (2013.01); *A61F 2002/0081* (2013.01); *A61F 2220/0016* (2013.01); *A61F 2230/0065* (2013.01)

(58) Field of Classification Search
CPC .... A61F 2/2442; A61F 2/2445; A61F 2/2448; A61F 2/2466
See application file for complete search history.

(56) References Cited

U.S. PATENT DOCUMENTS

| | | | |
|---|---|---|---|
| 2012/0123531 A1 | 5/2012 | Tsukashima et al. | |
| 2019/0053905 A1 | 2/2019 | Alon | |
| 2020/0163763 A1 | 5/2020 | Zipory et al. | |

FOREIGN PATENT DOCUMENTS

WO    2018035118 A1    2/2018

OTHER PUBLICATIONS

PCT/US2021/071468, International Search Report and Written Opinion, dated Jan. 19, 2022, 19 pages.

*Primary Examiner* — William H Matthews
(74) *Attorney, Agent, or Firm* — Dorsey & Whitney LLP (57) ABSTRACT

The present disclosure relates to methods and systems for aligning annuloplasty rings during surgical procedures and selectively engaging portions of the targeted annuli. Specifically, the disclosure is directed to methods and systems for aligning an annuloplasty ring or a toroidal portion thereof with natural fiducials present at or near an annular target, and engaging the annulus at the points aligned with the natural fiducials.

38 Claims, 12 Drawing Sheets

ANNULI ENGAGEMENT AND RESHAPING USING NATURAL FIDUCIALS

RELATED CASES

This application is a 35 U.S.C. 371 National Phase application claiming priority to PCT/US2021/071468, filed Sep. 15, 2021, which claims priority to U.S. Provisional Application No. 63/078,759, filed on Sep. 15, 2020, and titled "ANNULI ENGAGEMENT AND RESHAPING USING NATURAL FIDUCIALS," both of which are hereby incorporated by reference in their entirety.

BACKGROUND

The present disclosure is directed to methods and systems for aligning annuloplasty rings during surgical procedures and selectively engaging portions of the targeted annuli. Specifically, the disclosure is directed to methods and systems for aligning an annuloplasty ring or a toroidal portion thereof with natural fiducials present at or near an annular target, and engaging the annulus at the points aligned with the natural fiducials.

Annuloplasty remains a fundamental component in heart valve repair. The annuloplasty ring may be used to restore the size and shape of the native annulus; to prevent future annular dilatation; and to provide functional annular support.

For example, dilation of the annulus of the mitral valve (MV) prevents the valve leaflets from fully coapting when the valve is closed, leading to mitral regurgitation (MR) of blood from the left ventricle into the left atrium.

Under typical circumstances, in MV repair using ring annuloplasty, in which a docking member is anchored to the annulus, drastically reduces the mobility of the central posterior leaflet, causing valve closure to be a single anterior leaflet process with a frozen posterior buttress. Accordingly, and to ensure full cooptation of the leaflets, it is advantageous to properly locate the annuloplasty ring within the annulus.

Similarly, tricuspid regurgitation (TR) of the tricuspid valve (TV), is thought to affect a majority of the population in the U.S. Regardless, relatively few tricuspid valve operations are performed annually due to various challenges associated with surgical or percutaneous transcatheter based treatment of TR.

The proposed technology aims to address the shortcomings of the current systems.

SUMMARY

In an exemplary implementation, provided herein is a device operable to align to at least one natural fiducial of an annular target and engage a portion of the annular target at the location aligned with the at least one natural fiducial, the device comprising: an annuloplasty ring, or a first toroidal portion thereof, each having an outer hollow tube with a plurality of slotted backbone therein, the annuloplasty ring or its toroidal portion are each operable to change from an insertion configuration to an operable configuration; an alignment and engagement construction comprising at least one cannula, the cannula having a sleeve coupled to a distal end of the cannula, the sleeve being releasably coupled to the outer hollow tube via a coupling sub-assembly, the construction operable to align with and engage the at least one natural fiducial; and a delivery catheter having a proximal end and a distal end, adapted, sized and configured to accommodate: the alignment and engagement construction, the coupling assembly and the annuloplasty ring or the first toroidal portion thereof in its insertion configuration, and wherein the delivery catheter is operable, once the annuloplasty ring or its first toroidal portion is inserted, to alter the annuloplasty ring, or its first toroidal portion from the insertion configuration to the operable configuration.

In another exemplary implementation, provided herein is a method for aligning an annuloplasty ring or its first toroidal portion to at least one natural fiducial of an annular target and engage a portion of the annular target aligned with the at least one natural fiducial, implementable in a system comprising an annuloplasty ring, or a first toroidal portion thereof, each having an outer hollow tube with a plurality of slotted backbone therein, the annuloplasty ring or its toroidal portion are each operable to change from an insertion configuration to an operable configuration; an alignment and engagement construction comprising at least one cannula, the cannula having a sleeve coupled to a distal end of the cannula, the sleeve being releasably coupled to the outer hollow tube via a coupling sub-assembly, the construction operable to align with and engage the at least one natural fiducial; and a delivery catheter having a proximal end and a distal end, adapted, sized and configured to accommodate: the alignment and engagement construction, the coupling assembly and the annuloplasty ring or the first toroidal portion thereof in its insertion configuration, and wherein the delivery catheter is operable, once the annuloplasty ring or its first toroidal portion is inserted, to alter the annuloplasty ring or its first toroidal portion from the insertion configuration to the operable configuration, the method comprising: using the delivery catheter, introducing the annuloplasty ring or the first toroidal portion thereof to the annular target site; using the delivery catheter, altering the insertion configuration of the annuloplasty ring or the first toroidal portion thereof to the operable configuration; using the alignment and engagement construction, aligning the at least one sleeve with the at least one natural fiducial; engaging the annular target at the location aligned with the at least one natural fiducial; and releasing the sleeve from the outer hollow tube.

In yet another embodiment, the cannula comprises a harpoon operable to engage the natural fiducial, wherein the harpoon comprises: a self-penetrating tip; a foreshaft distally coupled to the self-penetrating tip, the foreshaft defining a radial aperture disposed along the foreshaft's longitudinal axis; a pushrod, having a proximal end defining an axial socket sized and releasably coupled to the distal end of the foreshaft; optionally, a tether looped through the radial aperture; and optionally, at least one spur, operably coupled to the self-penetrating head, configured to transition from a first insertion position to a second anchoring position.

In still yet another exemplary implementation, the annuloplasty ring or its first toroidal portion each has at least one anterior and one posterior zone, each zone comprising a plurality of internal anchor members located at least partially within the corresponding outer hollow tube, each anchor operable to selectably extend radially from the outer hollow tube and engage an anterior and a posterior portion of the annular target, wherein the method further comprises: retracting the delivery catheter to abut the posterior portion of the annulus; using the plurality of anchoring members in the posterior portion of the annuloplasty ring or its first toroidal portion, anchoring the annuloplasty ring or its first toroidal portion to the posterior portion of the annular target; using the tether, pulling the anchored posterior portion of the annulus toward the engaged (anterior) portion of the annulus; and using the plurality of anchoring members in the anterior portion of the annuloplasty ring or its first toroidal portion, anchoring the annuloplasty ring or its first toroidal portion to the anterior portion of the annular target.

In an exemplary implementation, provided herein is the use of a system operable to align an annuloplasty ring or its first toroidal portion to at least one natural fiducial of an annular target and engage a portion of the annular target aligned with the at least one natural fiducial, the system comprising: an annuloplasty ring or a first toroidal portion thereof, each having an outer hollow tube with a plurality of slotted backbone therein, the annuloplasty ring or its toroidal portion are each operable to change from an insertion configuration to an operable configuration; an alignment and engagement construction comprising at least one cannula, the cannula having a sleeve coupled to a distal end of the cannula, the sleeve being releasably coupled to the outer hollow tube via a coupling sub-assembly, the construction operable to align with and engage the at least one natural fiducial; and a delivery catheter having a proximal end and a distal end, adapted, sized and configured to accommodate: the alignment and engagement construction, the coupling assembly and the annuloplasty ring or the first toroidal portion thereof in its insertion configuration, and wherein the delivery catheter is operable, once the annuloplasty ring or its first toroidal portion is inserted, to alter the annuloplasty ring or its first toroidal portion from the insertion configuration to the operable configuration, in the process for aligning an annuloplasty ring, or its first toroidal portion to at least one natural fiducial of an annular target and engage a portion of the annular target aligned with the at least one natural fiducial, by performing the steps of: using the delivery catheter; introducing the annuloplasty ring or the first toroidal portion thereof to the annular target site; using the delivery catheter; altering the insertion configuration of the annuloplasty ring or the first toroidal portion thereof to the operable configuration; using the alignment and engagement construction, aligning the at least one sleeve with the at least one natural fiducial; engaging the annular target aligned with the at least one fiducial; and releasing the sleeve from the outer hollow tube.

BRIEF DESCRIPTION OF THE DRAWINGS

The method implementable using the alignment and engagement systems disclosed herein will become apparent from the following detailed description when read in conjunction with the figures, which are exemplary, not limiting, and in which.

While the disclosure of the methods implementable using the alignment and engagement systems disclosed herein is amenable to various modifications and alternative forms, specifics thereof have been shown by way of example in the drawings and will be further described in detail below. It should be understood, however, that the intention is not to limit the disclosure to the particular exemplary implementations described. On the contrary, the intention is to cover all modifications, equivalents, and alternatives.

DETAILED DESCRIPTION

Provided herein are exemplary implementations of methods, systems, subsystems and kits for aligning an annuloplasty ring or its first toroidal portion to at least one natural fiducial of an annular target and engage a portion of the annular target aligned with the at least one natural fiducial. The annular target can be, for example: a pulmonary valve, a mitral valve, a tricuspid valve, and an aortic valve.

Furthermore, and as is typically the case, the three dimensional profile of the annulus in some of these valves is dynamic during the cardiac cycle absent implantation of the annuloplasty ring or its toroidal portion, making proper alignment using the methods and systems disclosed beneficial for proper operation of the valves. Furthermore, in the context of the disclosure, the term annuloplasty ring, or its toroidal portion does not necessarily mean a ring defining a single plane, but rather encompasses other planes, for example, a saddle-shaped ring.

Likewise, the term "its (first, second) toroidal portion" means, in the context of the disclosure, any part of the ring operable to be adjoined to form the full annuloplasty ring. For example, in certain implementations, the toroidal portion can be less than half the full ring, or less than a quarter of the full ring and be operable to adjoin other components and form the full annuloplasty ring.

Definitions

The term "coupled," including its various forms such as "operably coupling," "coupling" or "couplable," refers to and comprises any direct or indirect structural coupling, connection or attachment, or adaptation or capability for such a direct or indirect structural or operational coupling, connection or attachment, including integrally formed components and components which are coupled via or through another component or by the forming process. Indirect coupling may involve coupling through an intermediary member or adhesive, or abutting and otherwise resting against, whether frictionally or by separate means without any physical connection.

In addition, for the purposes of the present disclosure, directional or positional terms such as "top," "bottom," "upper," "lower," "side," "front," "frontal," "forward," "rear," "rearward," "back," "trailing," "above," "below," "left," "right," "radial," "vertical," "upward," "downward," "outer," "inner," "exterior," "interior," "intermediate," "apical," "basal," etc., are merely used for convenience in describing the various exemplary implementations of the present disclosure.

Likewise, the term "engage" and various forms thereof, when used with reference to an engaging element, for example in the engagement of washer 302 in docking member 301 between the pair release cords 103, refers in an exemplary implementation to the application of any forces that tend to hold docking member 301 and a pair of release cords 103 together against inadvertent or undesired separating forces (e.g., such as may be introduced during alignment/engagement and manipulation of the annuloplasty ring or its toroidal portion). It is to be understood, however, that engagement does not in all cases require an interlocking connection that is maintained against every conceivable type or magnitude of separating force. Further, the term "engaging element" refers in another exemplary implementation to one or a plurality of coupled components, at least one of which is configured for releasably engaging another element. Thus, this term encompasses both single part engaging elements and multi-part assemblies, for example, coupling assembly 303 as a whole.

The terms "first," "second," and the like herein do not denote any order, quantity, or importance, but rather are used to denote one element from another. The terms "a," "an" and "the" herein do not denote a limitation of quantity, and are to be construed to cover both the singular and the plural, unless otherwise indicated herein or clearly contradicted by context. The suffix "(s)" as used herein is intended to include both the singular and the plural of the term that it modifies, thereby including one or more of that term (e.g., lance-member(s) 2014j includes one or more lance members).

Reference throughout the specification to "one exemplary implementation," "another exemplary implementation," "an exemplary implementation," and so forth, means that a particular element (e.g., step, feature, structure, and/or characteristic) described in connection with the exemplary implementation is included in at least one exemplary implementation described herein, and may or may not be present in other exemplary implementations. In addition, it is to be understood that the described elements may be combined in any suitable manner in the various exemplary implementations.

In the context of the disclosure, the term "operable" means the system and/or the device, or a certain element or step is fully functional, sized, adapted and calibrated, comprises elements for, and meets applicable operability requirements to perform a recited function when activated, coupled, implemented, actuated, effected, or realized. In relation to systems, the term "operable" means the system is fully functional and calibrated, having the necessary elements, as well as the mechanisms for, and meets applicable operability requirements to perform a recited function when executed by a user.

The term "abut" refers in the context of the disclosure, to items that are in direct physical contact with each other, although the items may not be attached, secured, fused, glued, sewn, or welded together.

In the context of the disclosure, the term "natural fiducial" is used to describe an identifiably distinctive anatomical feature including, without limitation, the right fibrous trigon, left fibrous trigon, interleaflet triangle, tricuspid posterior-anterior hinge, or a combination comprising one or more of the foregoing.

In the context of the disclosure, the term "aligned" is a broad term and is generally meant to include, without limitation, having a fixed angular relationship between about 0 degrees and about 180 degrees between at least one alignment and engagement construction, the delivery catheter, or a marker on the annuloplasty ring or its toroidal portion, and at least one natural fiducial.

In the context of the disclosure, the term "saddle-shaped" is used herein to mean an annuloplasty ring generally made of two arcuate members, for example, two toroidal portions with each toroidal portion having an apex and two ends connecting the toroidal portions. The apex of the toroidal portion in one member can be in the same or opposite direction of the other member. The formed ring can be generally D-shaped.

A more complete understanding of the methods, systems, subsystems and kits for aligning an annuloplasty ring or its first toroidal portion to at least one natural fiducial of an annular target and engaging the portion of the annular target aligned with the at least one natural fiducial can be obtained by reference to the accompanying drawings. These figures (also referred to herein as "FIGS.") are merely schematic representations based on convenience and the ease of demonstrating the present disclosure, and are, therefore, not intended to indicate relative size, scale and dimensions of the devices or components thereof, and/or to define or limit the scope of the exemplary implementations. Although specific terms are used in the following description for the sake of clarity, these terms are intended to refer only to the particular structure of the exemplary implementations selected for illustration in the drawings, and are not intended to define or limit the scope of the disclosure. In the drawings and the following description below, it is to be understood that like numeric designations refer to components of like function.

Figure 1:
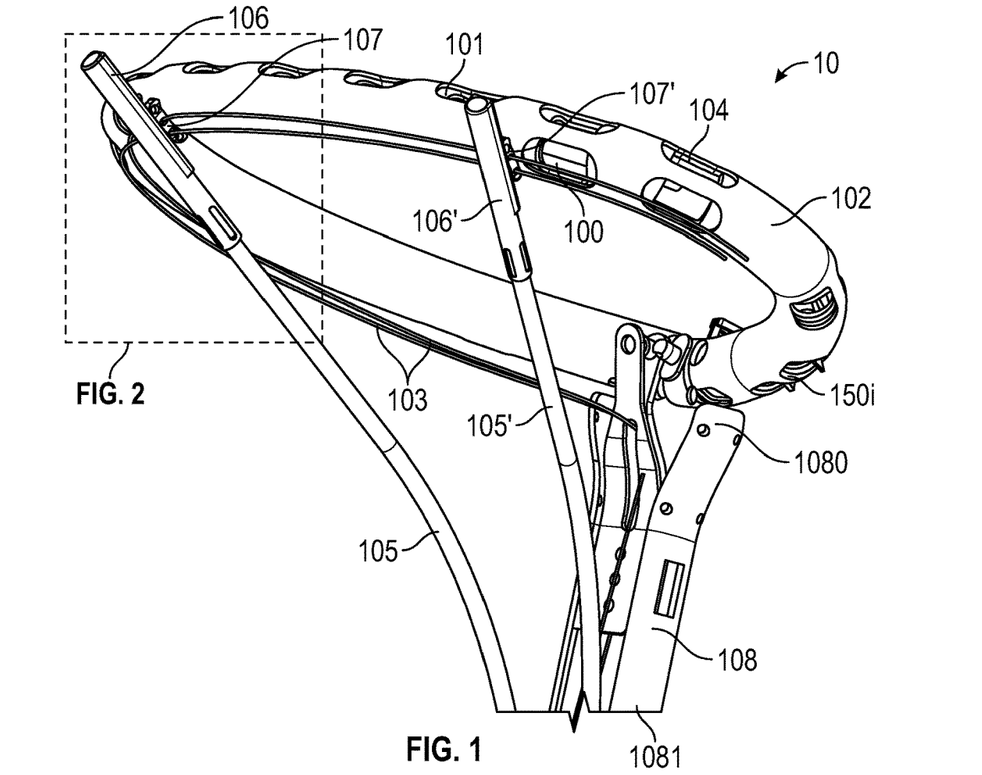
FIG. 1 illustrates an exemplary implementation of the alignment and engagement device.
Figure 2:
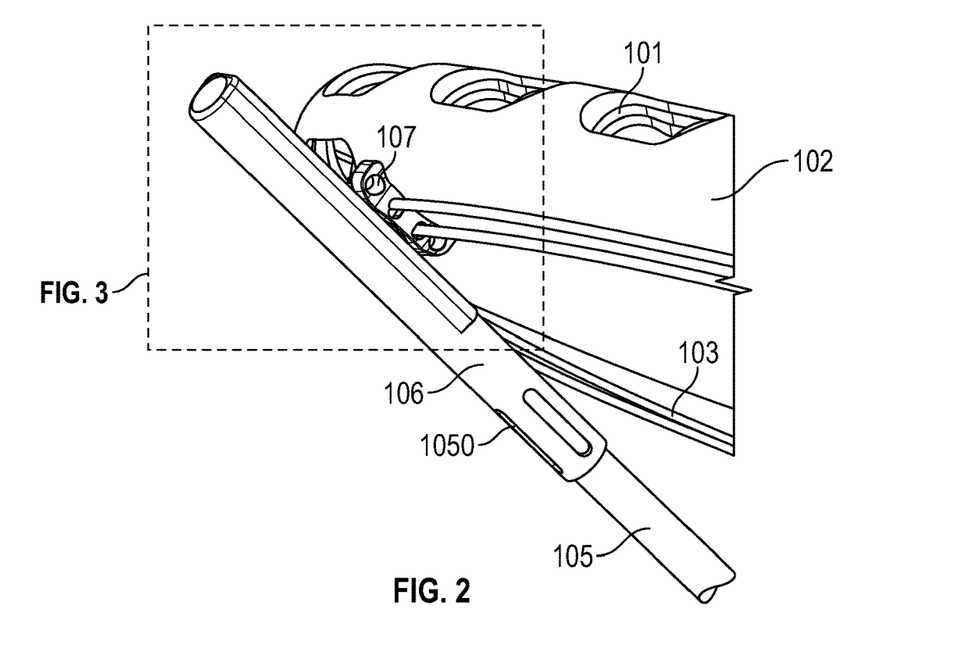
FIG. 2 illustrates an enlarged portion from FIG. 1 showing the releasable attachment.
Figure 3:
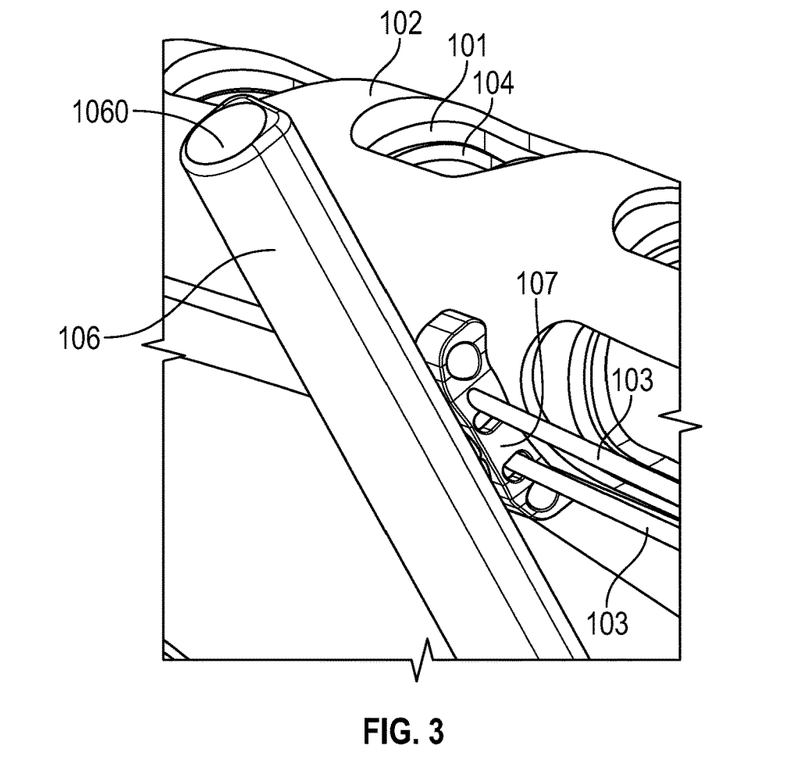
FIG. 3 illustrates the enlarged portion from FIG. 2 showing the releasable attachment in greater detail.
Figure 10A:
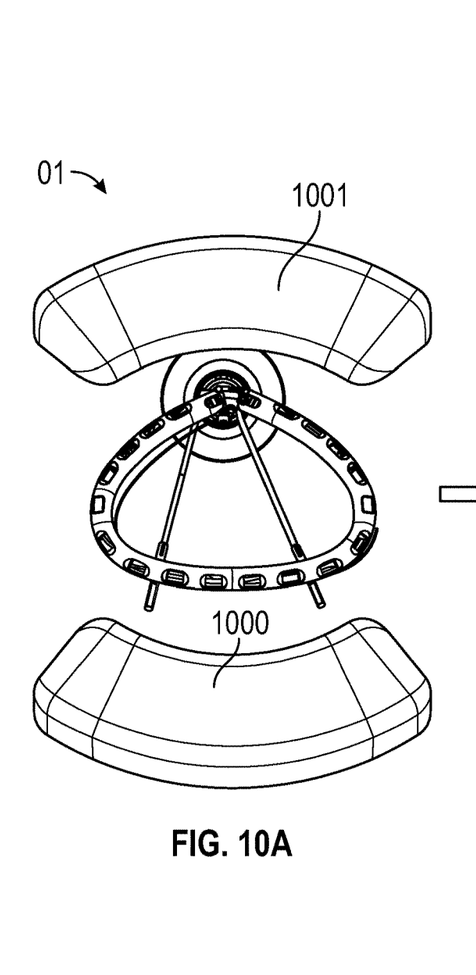
FIGS. 10A-10L are schematic illustrations of an exemplary implementation of the use of the devices disclosed, in the process of reshaping an annular target, by aligning to at least one natural fiducial of the annular target and engaging with the portion of the annular target aligned with the at least one natural fiducial.

FIGS. 1-3 illustrate an exemplary implementation of the alignment and engagement device. As illustrated, device 10 is operable to align to at least one natural fiducial (see, e.g., 511, 512, FIG. 11) of an annular target and engage a location of the portion of the annular target aligned with the at least one natural fiducial (see, e.g., 1000, FIG. 10A), device 10 comprising: an annuloplasty ring 100 or a first toroidal portion thereof, each having an outer hollow tube 101 with a plurality of slotted backbone 104 (see, e.g., FIG. 3) therein, annuloplasty ring 100 or its toroidal portion (not shown), with a plurality of segments formed by slotted ribbon 104 (see, e.g., commonly assigned U.S. application Ser. No. 16/702,338, filed Mar. 12, 2019 and titled "STABILIZING AND ADJUSTING TOOL FOR CONTROLLING A MINIMALLY INVASIVE MITRAL/TRICUSPID VALVE REPAIR SYSTEM," which is incorporated herein in its entirety), are each operable to change from an insertion configuration to an operable configuration; alignment and engagement construction comprising at least one cannula 105, 105', each cannula 105, 105' having sleeve 106, 106' coupled to distal end of cannula 105, 105', each sleeve being releasably coupled to outer hollow tube 101, or, in other exemplary implementations, to wrapper 102 via coupling sub-assembly 107, 107', the construction operable to align the at least one natural fiducial and engage the location of the portion of the annular target aligned with the at least one natural fiducial; and delivery catheter 108 having proximal end 1080 and distal end 1081, adapted, sized and configured to accommodate: the alignment and engagement construction, coupling sub-assembly 107, 107' and annuloplasty ring 100 or the first toroidal portion thereof in its insertion configuration, and wherein delivery catheter 108 is operable, once annuloplasty ring 100 or its first toroidal portion is inserted, to alter annuloplasty ring 100 or its first toroidal portion from the insertion configuration to the operable configuration. Also illustrated in FIGS. 1-3 are release cords 103 and anchors 150i, forming a portion of the one or more zones such as, for example, a posterior zone (as illustrated by element 150i in FIG. 1, 1501i in FIG. 10F, and 1502i in FIG. 10H), each zone comprising a plurality of internal anchor members 1501i, 1502' located at least partially within outer hollow tube 101, the zones of the annuloplasty ring, or the second toroidal portion thereof disposed opposite (e.g., 1502' location) the alignment and engagement construction, each it h anchor 150i operable to selectably extend radially from outer hollow tube 101 and engage portion 1000, 1001 (see, e.g., FIG. 10A) of the annular target.

Figure 4:
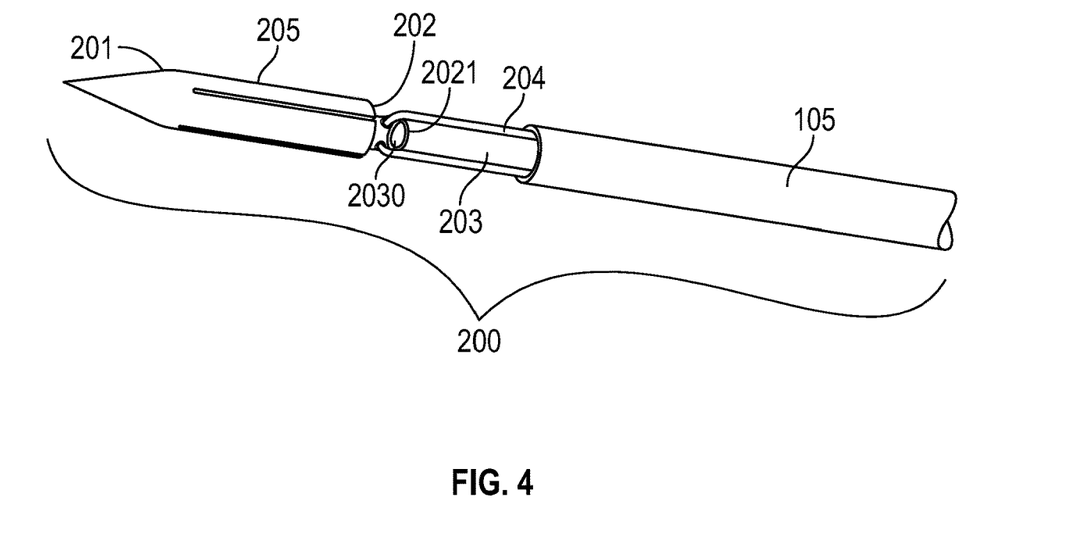
FIG. 4 illustrates an exemplary implementation of a harpoon used to engage a portion of the target annulus aligned with the natural fiducials.
Figure 5A:
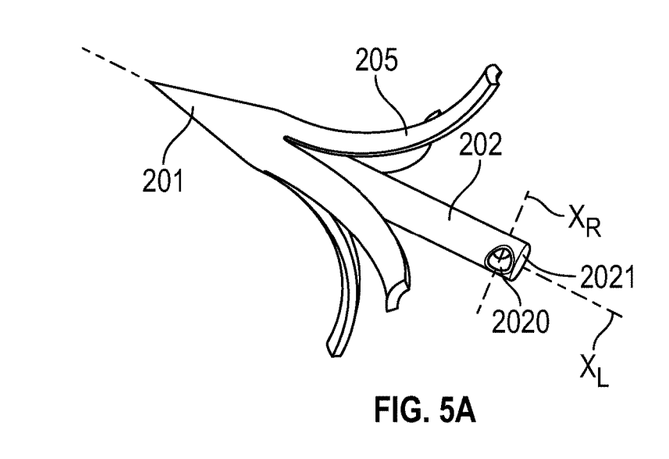
FIGS. 5A-5D illustrate a number of exemplary implementations of harpoon heads.
Figure 10B:
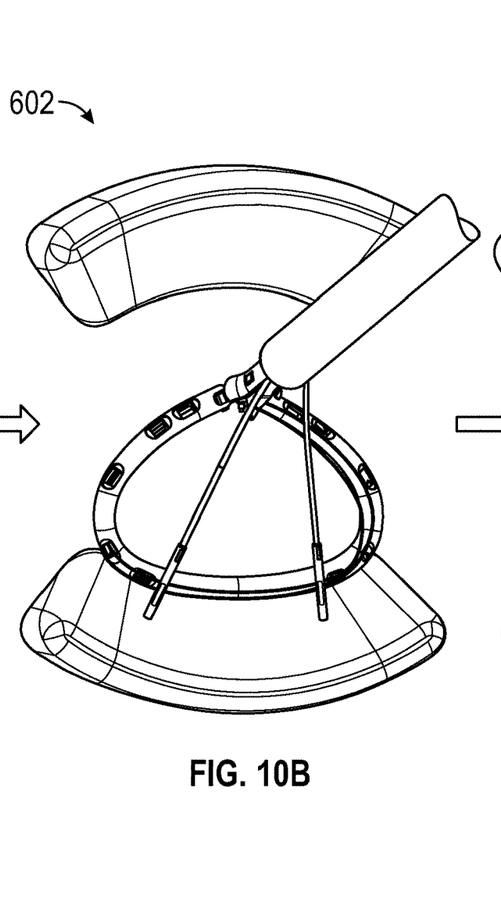
Figure 10C:
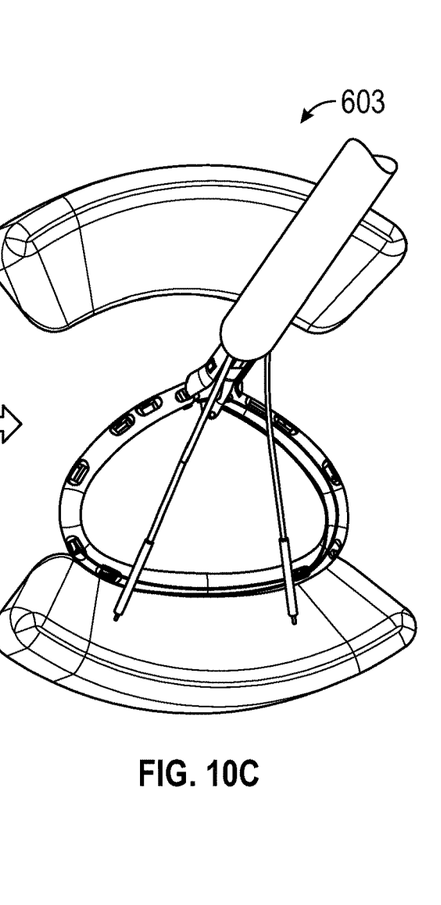
Figure 10D:
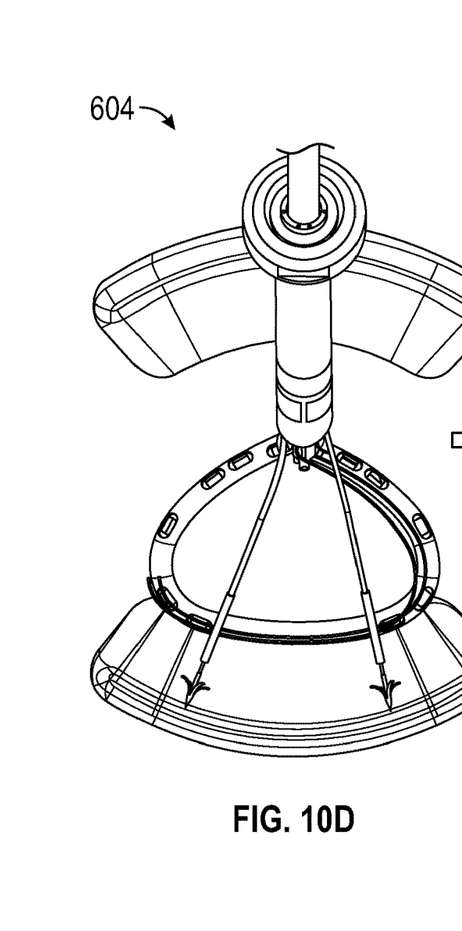
Figure 11:
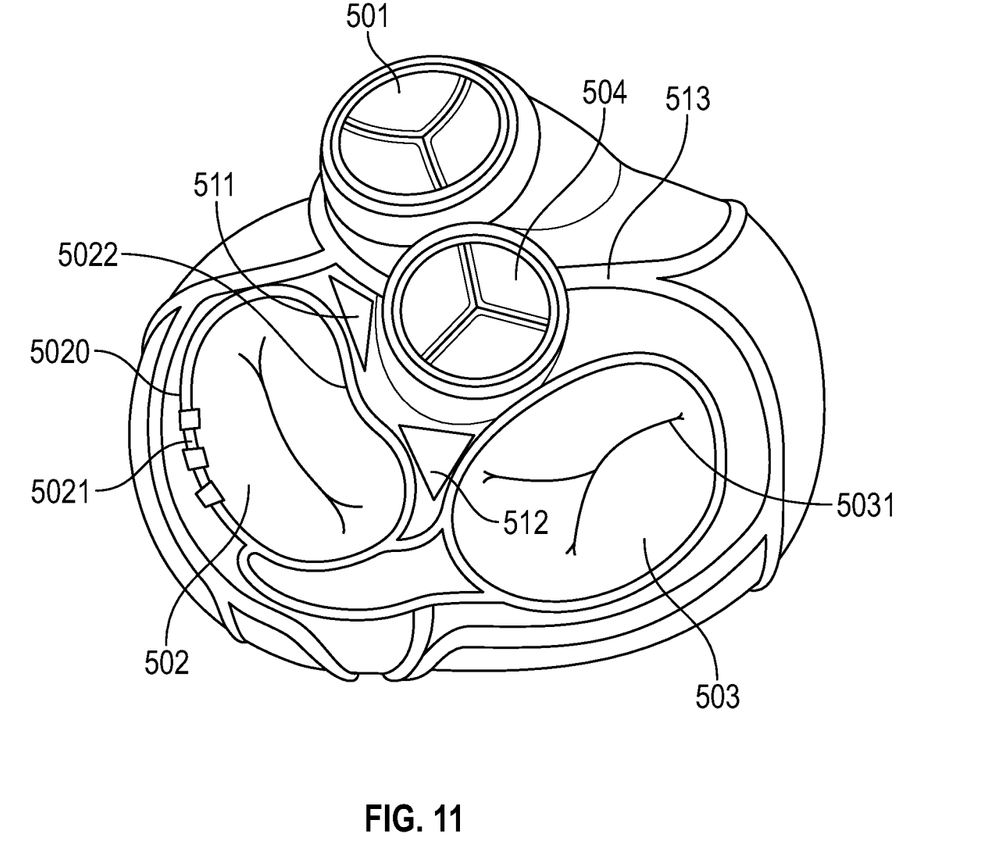
FIG. 11 is a schematic illustration of the heart valves including certain examples of natural fiducials.

FIG. 4 illustrates each cannula 105, 105' as comprising harpoon 200 operable to engage the portion of the annular target, at a location aligned with the at least one natural fiducial (see, e.g., 511, 512, FIG. 11, and FIG. 10D). As illustrated, in an exemplary implementation, harpoon 200 comprises: self-penetrating tip 201; foreshaft 202 distally coupled to self-penetrating tip 201; foreshaft 202 defining radial (XR) aperture 2020 disposed along the foreshaft 202 longitudinal axis XL; pushrod 203, having a proximal end defining axial socket 2030 sized to accommodate a (distal) portion of foreshaft 202, releasably coupled to the distal end 2021 (see, e.g., FIG. 5A) of foreshaft 202; optionally, tether 204 looped through radial aperture 2020; and optionally, at least one spur 205, operably coupled to the self-penetrating tip, configured to transition from a first insertion position (see, e.g., FIG. 4) to a second anchoring position (see, e.g., FIGS. 5A, 10D). In certain exemplary embodiments, pushrod 203 is a hollow tube, operable to both accommodate optional tether 204, or additionally, or alternatively, deliver other structural members, compositions and the like, to the engagement site, as well as remove portions of the engagement site.

In certain exemplary implementations, each sleeve 106, 106' used in the devices disclosed for implementing the methods provided, is sized and configured to accommodate self-penetrating tip 201, foreshaft 202, and optionally, at least one spur 205.

Figure 5B:
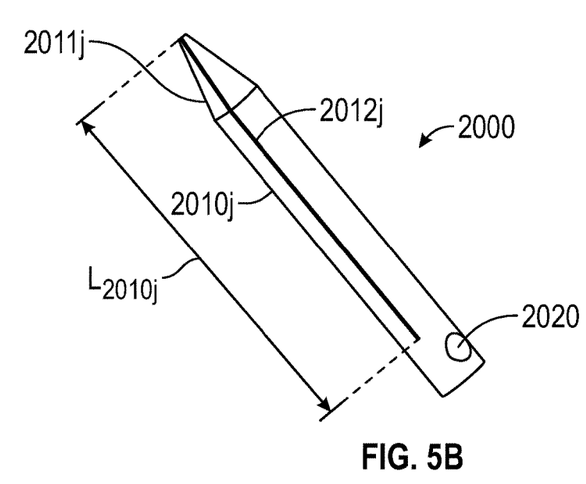
Figure 5C:
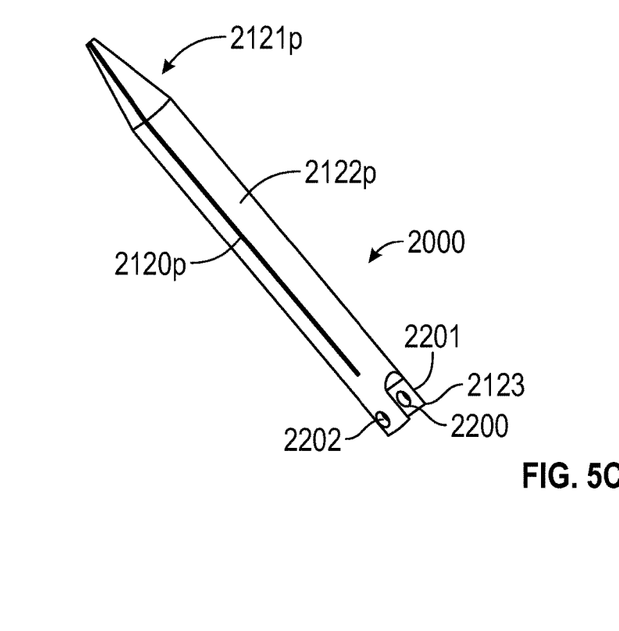
Figure 5D:
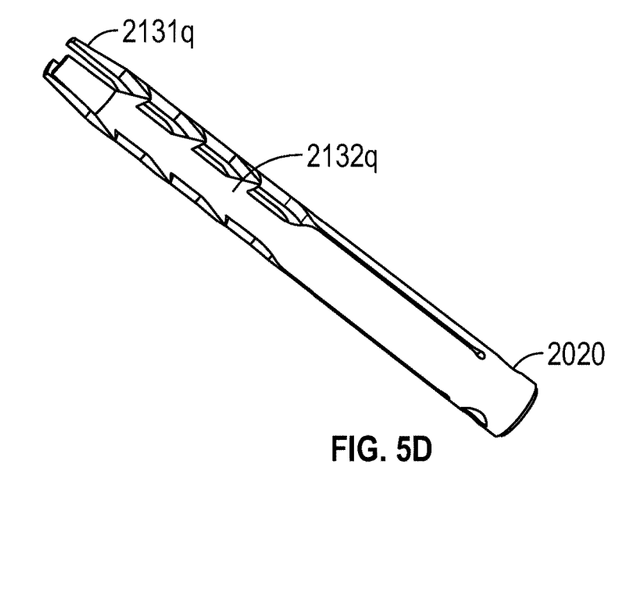
Figure 6A:
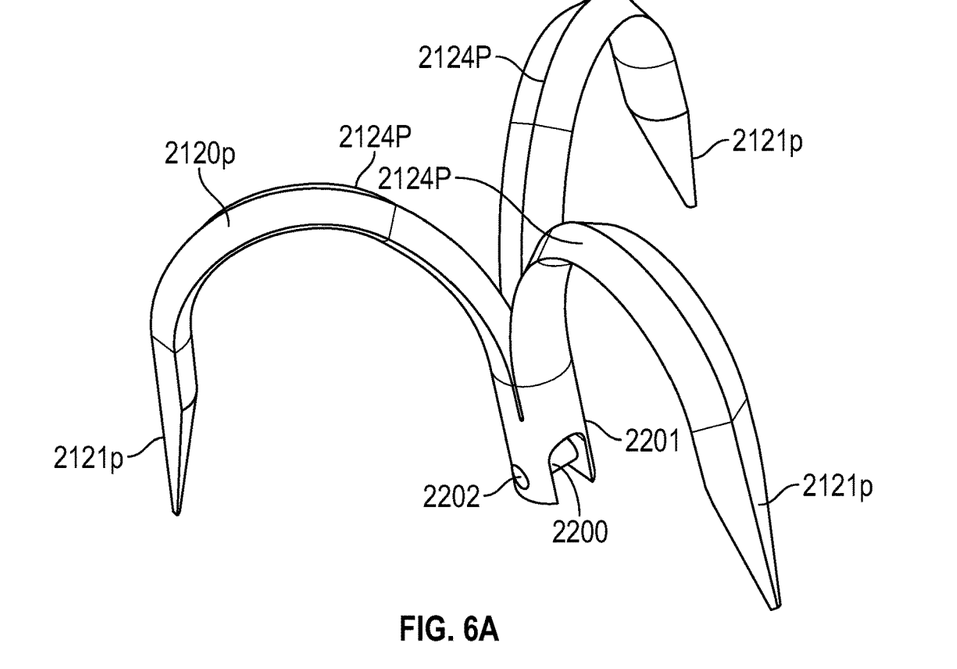
FIGS. 6A, 6B illustrate exemplary implementations of the multi-lance harpoon head illustrated in FIG. 5C following actuation.
Figure 6B:
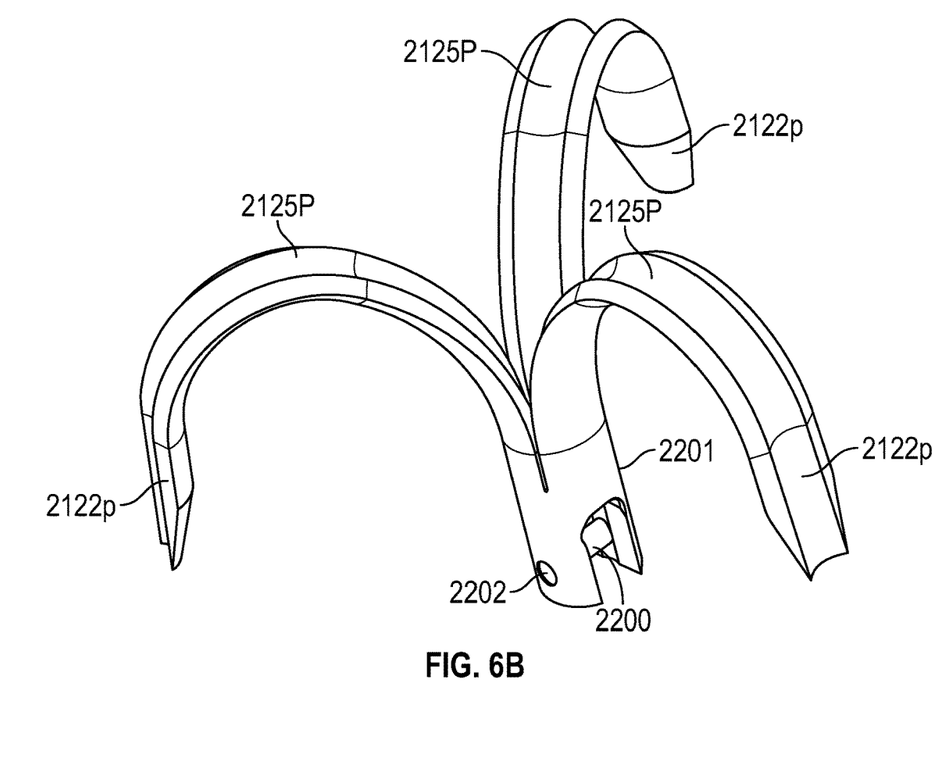

Under certain circumstances, and as illustrated in FIGS. 5B-7B, self-penetrating tip 201, foreshaft 202 and at least one spur 205 are all integrated to single penetrating head 2000, wherein single penetrating head 2000 is operable to transition between an insertion configuration as illustrated in FIGS. 5B, 5C and an anchoring configuration as illustrated in FIGS. 6A-7B. As illustrated in FIGS. 5B-7B, single penetrating head 2000 comprised of a plurality of lancing members (in other words, a multi-lance split tip), configured to have a cross section 2124p, 2014j operable to form filled cylinder single penetrating head 2000 in the insertion configuration, the filled cylinder having a conical tip 2121p, 2011j (see, e.g., FIGS. 6A, 7A, 7B). Additionally, or alternatively, in certain exemplary implementations, one or both harpoons 200 can be configured to comprise single penetrating head 2000 (multi-lance split tip) having a plurality of lancing members 2125p, configured to form, in the insertion configuration as illustrated in FIG. 6B, with a cross section 2124p, operable to form a hollow cylinder having a frustoconical conical tip 2122p. As illustrated in FIGS. 6A-8, upon actuation, each of the lancing members is configured to curve whereby tip 2011j, 2121p, 2131q of each lancing head is directed, in other words pointing to the distal end of a single penetrating head 2000.

Figure 7A:
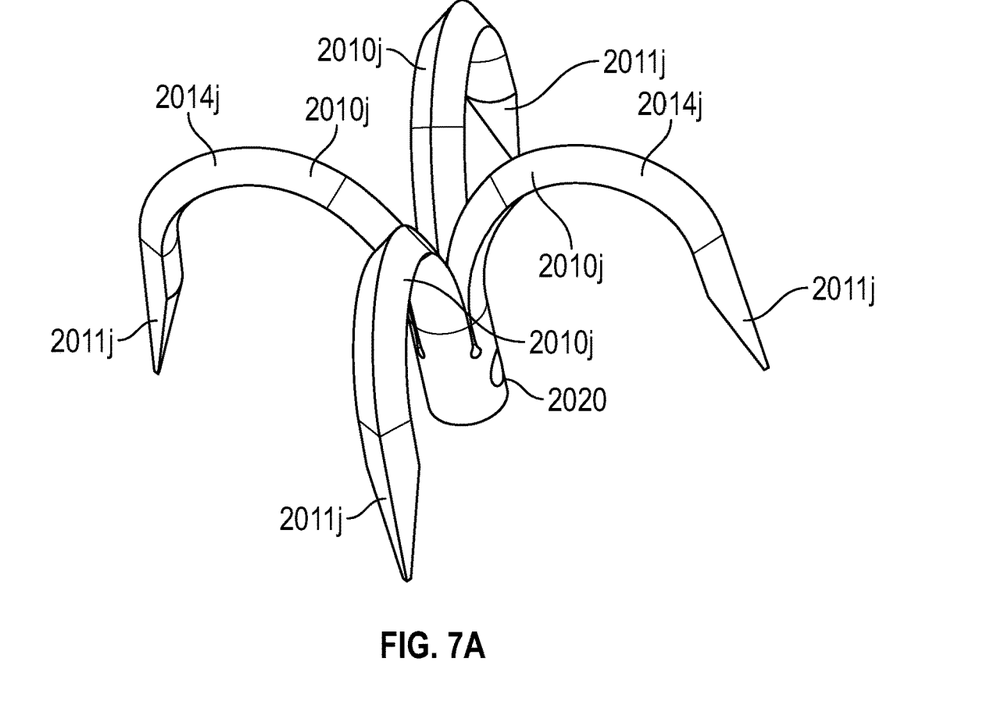
FIGS. 7A, 7B illustrate exemplary implementations of the multi-lance harpoon head illustrated in FIG. 5B following actuation.
Figure 7B:
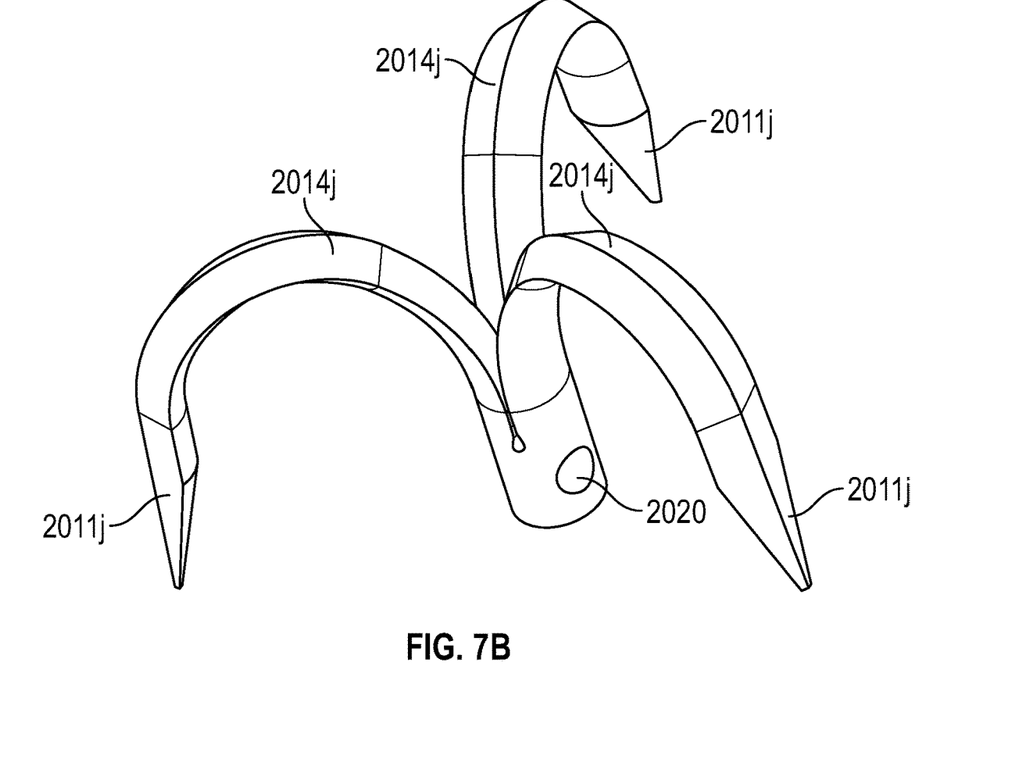
Figure 8:
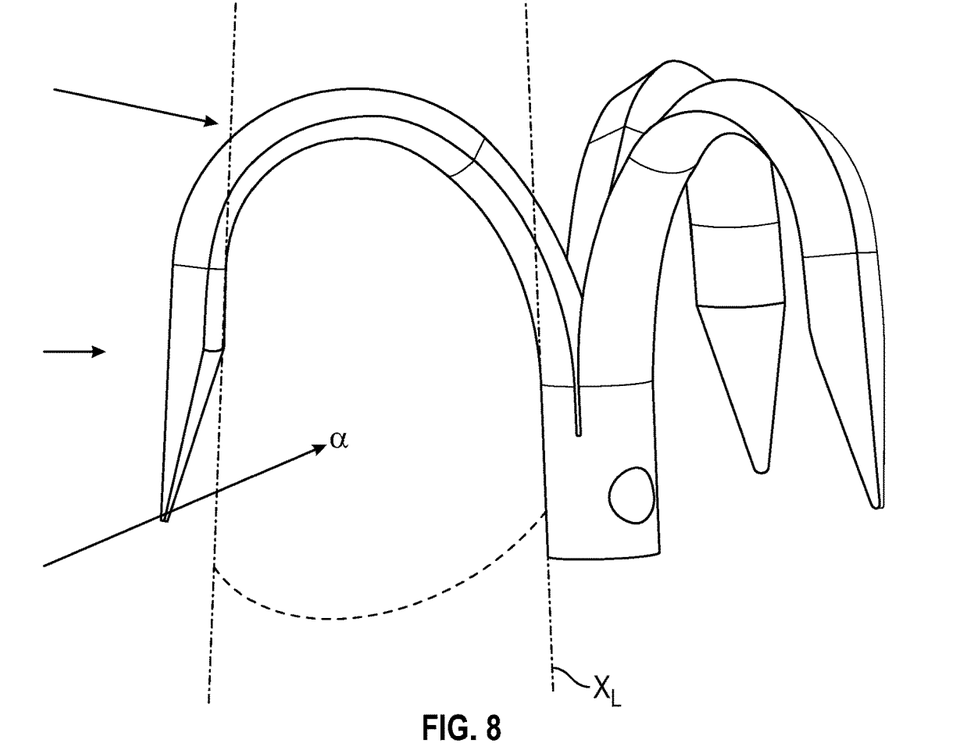
FIG. 8 illustrates an exemplary configuration of the multi-lance harpoon head of FIG. 7B.

As further illustrated in FIGS. 5B, 7B and 8, showing exemplary implementation of a single penetrating head 2000 comprised of a plurality of lancing members 2010j (in other words, a multi-lance split tip), configured to have a cross section 2124p, 2014j operable to form filled cylinder single penetrating head 2000 in the insertion configuration, the filled cylinder having a conical tip 2121p. When curved back, lancing members 2010j having a length of between about 0.01 mm and about 5.00 mm, are each configured to form angle a, defined between the tangent of each curved lancing member 2010j, and longitudinal axis XL of single penetrating head 2000.

Figure 9A:
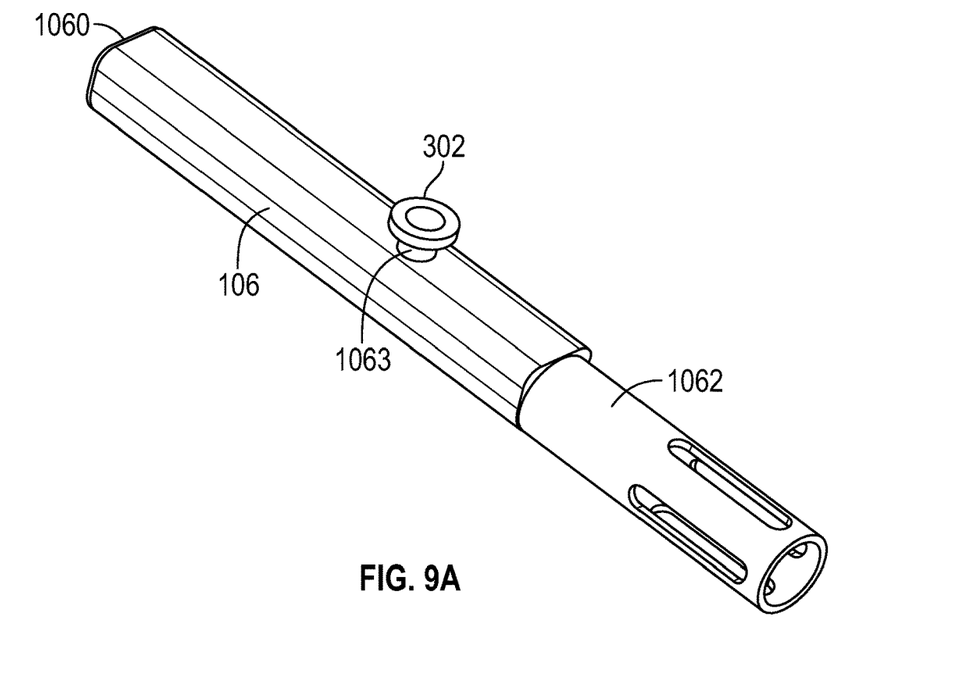
FIGS. 9A-9C illustrate the components of the alignment and engagement constructions, with FIG. 9A illustrating the sleeve, FIG. 9B illustrating the docking member and FIG. 9C illustrating the coupling of the sleeve to the docking member in the presence of the release cords.
Figure 9B:
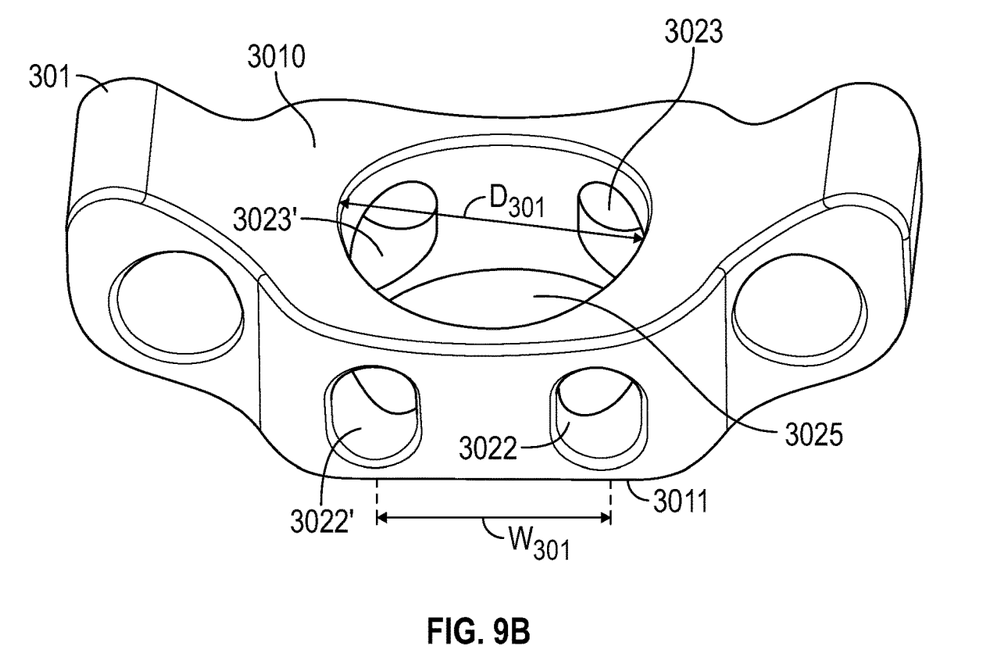
Figure 9C:
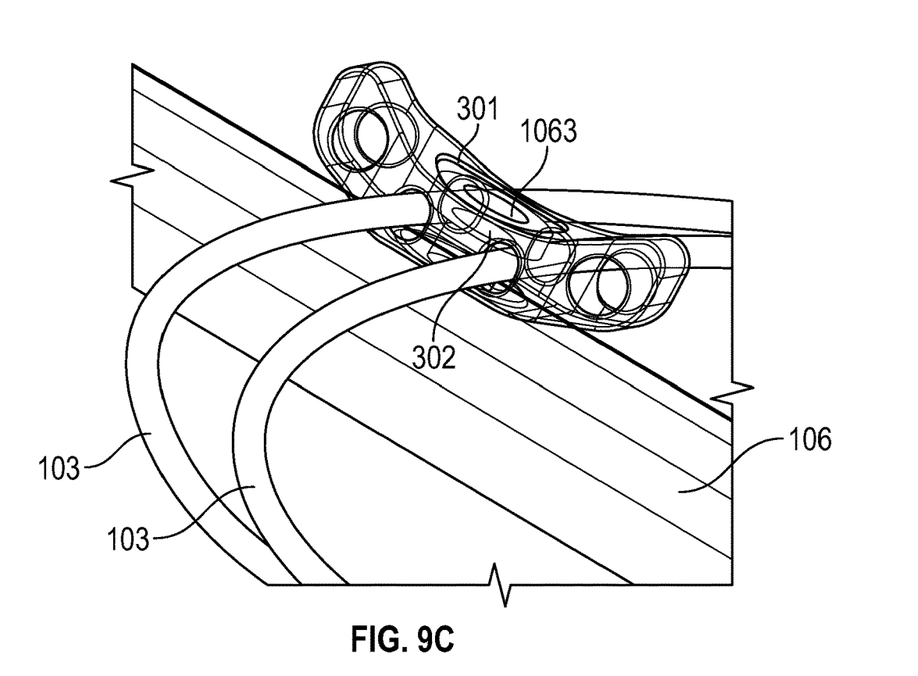

FIGS. 9A-9C illustrate the components of the alignment and engagement constructions, with FIG. 9A, illustrating sleeve 106, 106', FIG. 9B illustrating docking member 301, and FIG. 9C illustrating the releasable coupling sub-assembly 107, 107' of sleeve 106, 106' to docking member 301 in the presence of release cords 103. Accordingly, and as illustrated in FIG. 9A, each sleeve 106, 106' further comprises dorsal peg 1063 extending radially from each sleeve 106, 106', whereby each sleeve 106, 106' having open proximal end 1060, and open distal end 1062. Furthermore, each coupling sub-assembly 107, 107' comprises docking member 301 coupled to outer hollow tube 101, or wrapper 102, operable to releasably engage sleeve 106, 106'. As further illustrated in FIG. 9C, each coupling sub-assembly 107, 107' further comprises: washer 302, operably coupled to peg 1063, forming a flanged peg; and pair of release cords 103, wherein docking member 301 having arcuate apical surface 3010 with a diameter configured to abut the curvature of outer hollow tube 101 of annuloplasty ring 100, or its toroidal portion, docking member 301 further defines opening 3025 having a cylindrical internal surface with diameter D301 of between about 2.0 mm and about 5.0 mm, configured to accommodate the flanged peg, with two pairs 3022, 3022' and 3023, 3023' of diametrically aligned openings defined in docking member 301, the distance (W301) between each pair 3022, 3022' and 3023, 3023' sized and configured to be wider than the (dorsal) peg 1063 and narrower than the flange defined by washer 302 diameter, such that each pair of release cords 103 is threaded through the diametrically opposed openings 3022, 3022' and 3023, 3023' between the flange and sleeve 106, 106' (see, e.g., FIG. 9C).

In certain exemplary implementations, and as illustrated schematically in FIG. 11, the at least one natural fiducial is the right fibrous trigon 512, the left fibrous trigon 511, the interleaflet triangle (not shown), and the tricuspid posterioranterior hinge 5031, and wherein the annular target is at least one of: mitral valve 502, tricuspid valve 503, aortic valve 501, and pulmonary valve 504. For example, in an exemplary implementation, the annular target is mitral valve (MV) 502, the natural fiducials are right fibrous trigon 512 and left fibrous trigon 511 and wherein sleeves 106, 106' are radially spaced apart to align with right fibrous trigon 512 and left fibrous trigon 511, sequentially or simultaneously and engage anterior portion 5022 of mitral valve annulus 5020 at the location, or point of contact with anterior portion 5022 that is aligned with right fibrous trigon 512 and left fibrous trigon 511, see, e.g., FIG. 10D.

Figure 10E:
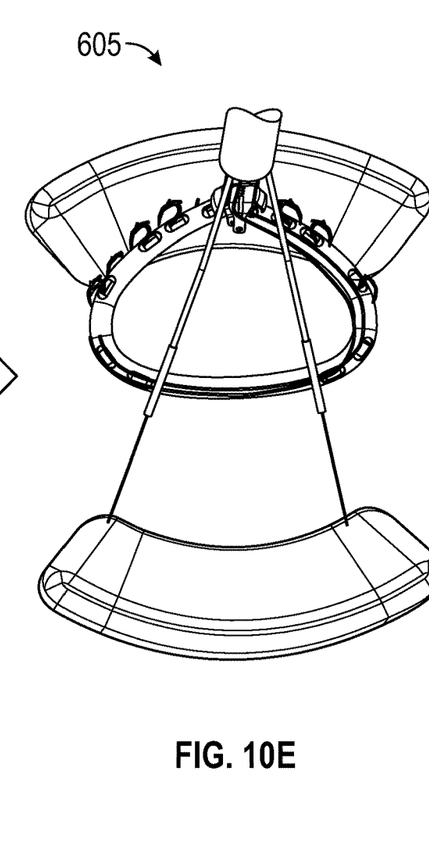
Figure 10F:
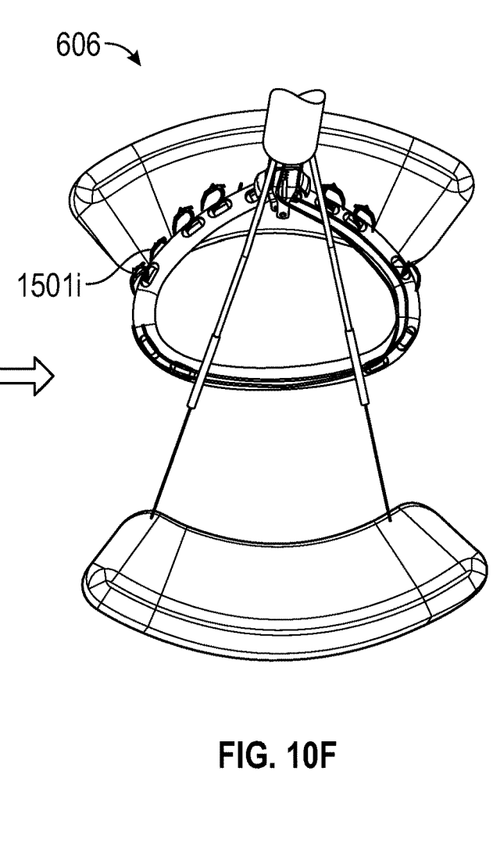
Figure 10G:
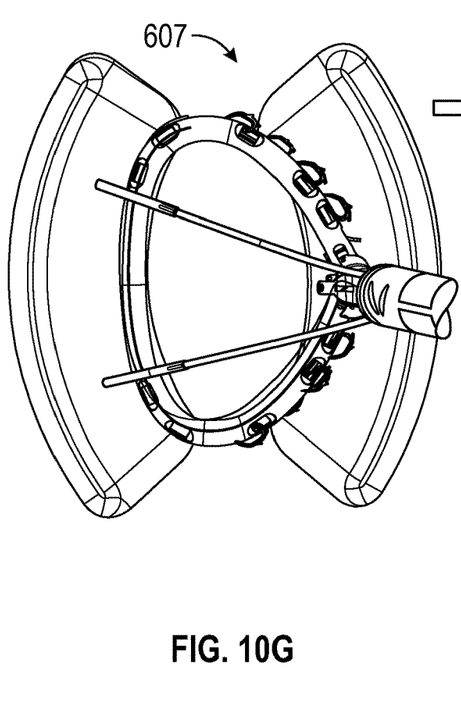
Figure 10H:
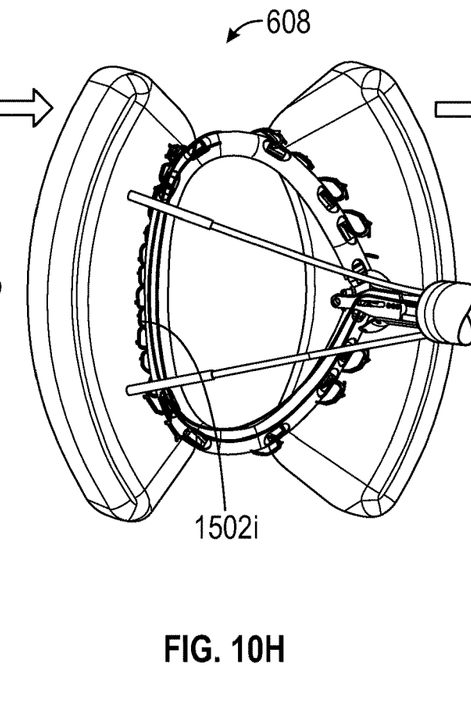
Figure 10I:
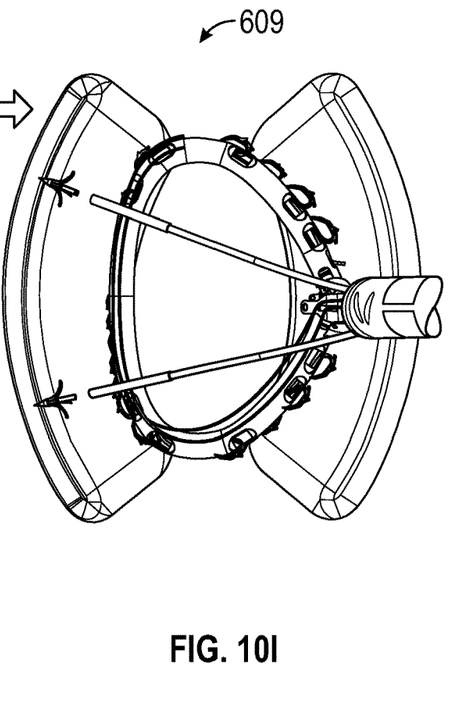
Figure 10J:
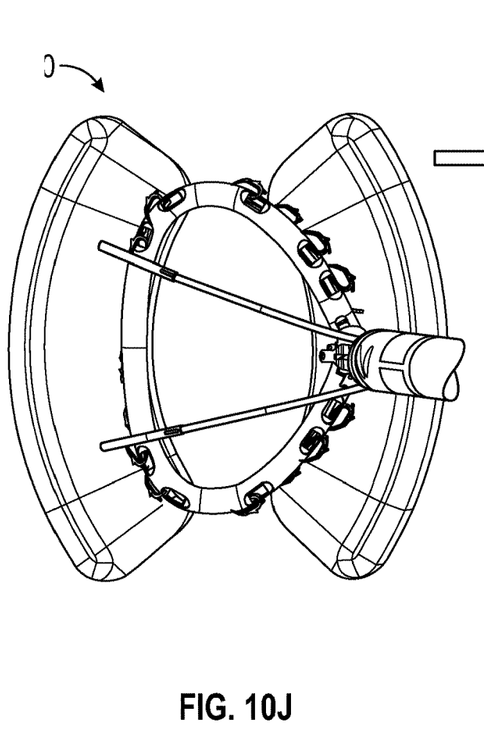
Figure 10K:
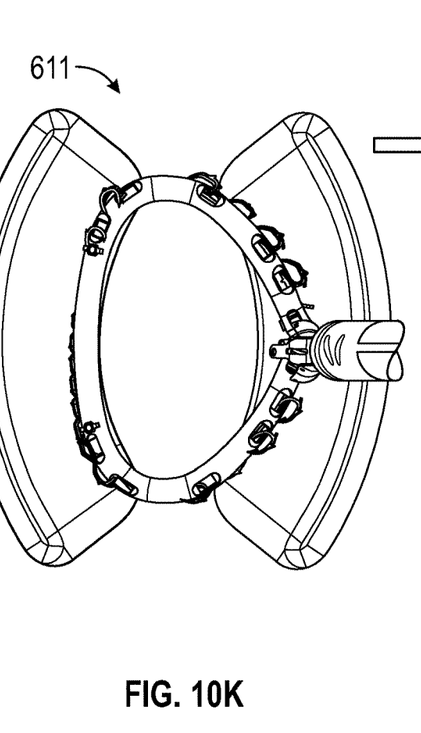
Figure 10L:
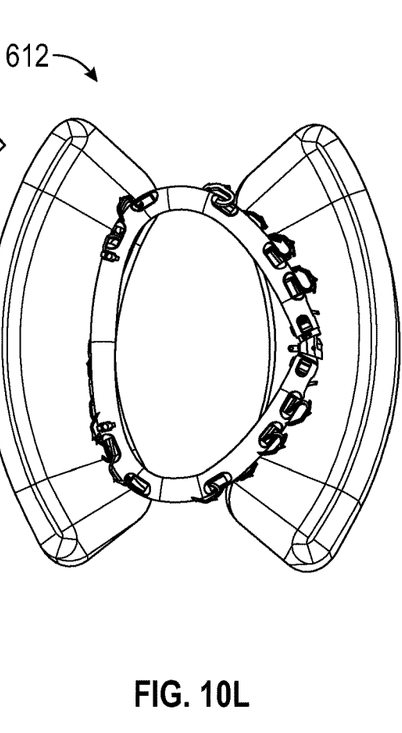

In an exemplary implementation, the methods disclosed herein are implemented using the devices and systems disclosed herein. Accordingly, provided herein is a method for aligning an annuloplasty ring, or its first toroidal portion to at least one natural fiducial of an annular target and engage a portion of the annular target aligned with the at least one natural fiducial, implementable in a system comprising an annuloplasty ring 100, or a first toroidal portion thereof, each having an outer hollow tube 101 with a plurality of slotted backbone 104 therein, the annuloplasty ring 100 or its toroidal portion are each operable to change from an insertion configuration to an operable configuration; an alignment and engagement construction comprising at least one cannula 105, 105, ' the cannula having a sleeve 106, 106' coupled to a distal end 1050 (see, e.g., FIG. 2) of the cannula 105, 105', the sleeve 106, 106' being releasably coupled to the outer hollow tube 101 via a coupling sub-assembly 107, 107', the construction operable to align the at least one natural fiducial (see, e.g., 511, 512, FIG. 11) and engage a portion of the annular target aligned with the at least one natural fiducial; and a delivery catheter 108 having a proximal end 1080 and a distal end 1081, adapted, sized and configured to accommodate: the alignment and engagement construction, the coupling sub-assembly 107, 107' and the annuloplasty ring 100 or the first toroidal portion thereof in its insertion configuration, and wherein the delivery catheter 108 is operable, once the annuloplasty ring 100 or its first toroidal portion is inserted, to alter the annuloplasty ring 100 or its first toroidal portion from the insertion configuration to the operable configuration, the method comprising: using the delivery catheter 108, introducing the annuloplasty ring 100 or the first toroidal portion thereof to the annular target site (see, e.g., 601, FIG. 10A); using the delivery catheter, altering the insertion configuration of the annuloplasty ring 100 or the first toroidal portion thereof to the operable configuration; using the alignment and engagement construction, aligning (see, e.g., 602, FIG. 10B) the at least one sleeve 106, 106' with the at least one natural fiducial (see, e.g., 511, 512, FIG. 11); engaging the annular target (see, e.g., 603, FIG. 10C) at the location aligned with the at least one natural fiducial (see, e.g., 511, 512, FIG. 11); and releasing the sleeve 106, 106' from the outer hollow tube 101. Furthermore, the step of engaging the annular target at the location aligned with the at least one natural fiducial comprises: using the pushrod 203, penetrating the location aligned with the at least one natural fiducial with the self-penetrating tip 201, wherein at least a portion of the foreshaft 202 remains external to the location aligned with the at least one natural fiducial; and optionally transitioning the at least one spur 205 to the anchoring position (see, e.g., FIGS. 5A, 10D). Likewise, the step of releasing the sleeve 106, 106' from the outer hollow tube 101 comprises: pulling the release cords 103; and using the delivery catheter 108, releasing the sleeve 106, 106' from the outer hollow tube (see, e.g., 610-612, FIGS. 10J-10L). In certain exemplary implementations, the method for aligning an annuloplasty ring or its first toroidal portion to at least one natural fiducial of an annular target and engage a portion of the annular target aligned with the at least one natural fiducial further comprises comprising: either simultaneously or sequentially, with releasing the pushrod from the foreshaft, using the delivery catheter 108, maneuvering (605, FIG. 10E) the one or more zones 1051*i*, each comprising the plurality of internal anchor heads 150*i* of the annuloplasty ring 100 or the second toroidal portion thereof to the posterior rim 5021 (see, e.g., FIG. 11) of the mitral valve 502; deploying (606, FIG. 10F) the anchors 1052*i* thereby engaging the posterior rim 5021 of the mitral valve 502; using tethers 204, pulling (607, FIG. 10G) the posterior rim 5021 of the mitral valve 502 toward the anterior rim 5022, aligned with natural fiducials 512, 511. Thereafter, deploying (608, FIG. 10H) the anchors 1052*i* configured to engage the anterior rim 5022 of the mitral valve 502; anchoring the anterior rim 5022 of the mitral valve 502 to the annuloplasty ring 100 or the first toroidal portion thereof; pulling (610, FIG. 10J) the release cords 103, thereby releasing the sleeve 106, 106' from the annuloplasty ring 100 or the first toroidal portion thereof; using the delivery catheter 108, retracting (611, FIG. 10K) each cannula 105, 105' and sleeve 106, 106'; and releasing (612, FIG. 10L) the annuloplasty ring 100 or the first toroidal portion thereof from the delivery catheter 108.

While in the foregoing specification the methods, systems, subsystems and kits for aligning an annuloplasty ring or a toroidal portion thereof with at least one natural fiducial in an annular target and engage a portion of the annular target at a location aligned with the at least one natural fiducials described herein have been described in relation to certain exemplary implementations, and many details are set forth for purposes of illustration, it will be apparent to those skilled in the art that the disclosure of the alignment methods, implementable using the systems disclosed herein, are susceptible to additional implementations and that certain of the details described in this specification and as are more fully delineated in the following claims can be varied considerably without departing from the basic principles disclosed herein.

What is claimed:

1. A device operable to align to at least one natural fiducial of an annular target and engage a portion of the annular target aligned with the at least one natural fiducial, the device comprising:

an annuloplasty ring, or a first toroidal portion thereof, each having an outer hollow tube comprising a backbone with a plurality of slots therein, the annuloplasty ring or a toroidal portion thereof are each operable to change from an insertion configuration to an operable configuration;

an alignment and engagement construction comprising at least one cannula, each cannula of the at least one cannula having a sleeve coupled to a distal end of the cannula, the sleeve being releasably coupled to the outer hollow tube via a coupling sub-assembly, the construction operable to align with the at least one natural fiducial and engage a portion of the annular target aligned with the at least one natural fiducial; and a delivery catheter having a proximal end and a distal end, adapted, sized and configured to accommodate: the alignment and engagement construction, the coupling sub-assembly and the annuloplasty ring or the first toroidal portion thereof in the insertion configuration, and wherein the delivery catheter is operable, once the annuloplasty ring or the first toroidal portion is inserted, to alter the annuloplasty ring or the first toroidal portion from the insertion configuration to the operable configuration.

2. The device of claim 1, wherein each cannula of the at least one cannula comprises a harpoon operable to engage a portion of the annular target aligned with the at least one natural fiducial.

3. The device of claim 2, wherein the harpoon comprises:
a self-penetrating tip;
a foreshaft distally coupled to the self-penetrating tip, the foreshaft defining a radial aperture disposed along a longitudinal axis of the foreshaft;
a pushrod, having a proximal end defining an axial socket sized to accommodate a portion of the foreshaft, releasably coupled to a distal end of the foreshaft;
optionally, a tether looped through the radial aperture; and optionally, at least one spur, operably coupled to the self-penetrating tip, configured to transition from a first insertion position to a second anchoring position.

4. The device of claim 3, wherein each sleeve is sized and configured to accommodate the self-penetrating tip, the foreshaft, and optionally, the at least one spur.

5. The device of claim 4, wherein each sleeve further comprises a dorsal peg extending radially from the sleeve.

6. The device of claim 5, wherein each coupling sub-assembly comprises a docking member coupled to the outer hollow tube, operable to releasably engage the sleeve.

7. The device of claim 6, wherein each coupling sub-assembly further comprises:
a washer, operably coupled to the peg, forming a peg with a flange; and
a pair of release cords, wherein the docking member further defines an opening having a cylindrical internal surface, configured to accommodate the peg, with two pairs of diametrically aligned openings defined in the docking member, a distance between each pair sized and configured to be wider than the peg and narrower than the flange, such that the pair of release cords is each threaded through the diametrically opposed openings between the flange and the sleeve.

8. The device of claim 7, wherein the pair of release cords are operably coupled to the proximal end of the delivery catheter.

9. The device of claim 1, wherein the at least one natural fiducial is at least one of a right fibrous trigon, a left fibrous trigon, an interleaflet triangle, and a tricuspid posterior-anterior hinge.

10. The device of claim 9, wherein the annular target is at least one of: a mitral valve, a tricuspid valve, an aortic valve, and a pulmonary valve.

11. The device of claim 10, wherein the annular target is the mitral valve, the natural fiducials are the right fibrous trigon and the left fibrous trigon and wherein the sleeves are radially spaced to align with the right fibrous trigon and the left fibrous trigon, sequentially or simultaneously and engage an anterior portion of a mitral valve annulus at the location aligned with the right fibrous trigon and the left fibrous trigon.

12. The device of claim 3, wherein the self-penetrating tip, the foreshaft and the at least one spur are integrated into a single penetrating head.

13. The device of claim 12, wherein the single penetrating head is operable to transition between an insertion configuration and an anchoring configuration.

14. The device of claim 13, wherein the single penetrating head is comprised of a plurality of lancing members, configured to form a filled cylinder having a conical tip.

15. The device of claim 13, wherein the single penetrating head is comprised of a plurality of lancing members, configured to form a hollow cylinder having a frusto-conical conical tip.

16. The device of claim 14, wherein upon actuation, each lancing member of the plurality of lancing members is configured to curve whereby the tip of each lancing member is directed to a distal end of the single penetrating head.

17. A method for aligning an annuloplasty ring or a first toroidal portion thereof to at least one natural fiducial of an annular target and engage a portion of the annular target aligned with the at least one natural fiducial, implementable in a system comprising an annuloplasty ring, or a first toroidal portion thereof, each having an outer hollow tube comprising a backbone with a plurality of slots therein, the annuloplasty ring or the toroidal portion are each operable to change from an insertion configuration to an operable configuration; an alignment and engagement construction comprising at least one cannula, each cannula of the at least one cannula having a sleeve coupled to a distal end of the cannula, the sleeve being releasably coupled to the outer hollow tube via a coupling subassembly, the construction operable to align with the at least one natural fiducial and engage a portion of the annular target aligned with the at least one natural fiducial; and a delivery catheter having a proximal end and a distal end, adapted, sized and configured to accommodate: the alignment and engagement construction, the coupling sub-assembly and the annuloplasty ring or the first toroidal portion thereof in the insertion configuration, and wherein the delivery catheter is operable, once the annuloplasty ring or the first toroidal portion is inserted, to alter the annuloplasty ring or the first toroidal portion from the insertion configuration to the operable configuration, the method comprising:
using the delivery catheter, introducing the annuloplasty ring or the first toroidal portion thereof to an annular target site;
using the delivery catheter, altering the insertion configuration of the annuloplasty ring or the first toroidal portion thereof to the operable configuration;
using the alignment and engagement construction, aligning the at least one sleeve with the at least one natural fiducial;
engaging the annular target at the location aligned with the at least one natural fiducial; and
releasing the sleeve from the outer hollow tube.

18. The method of claim 17, wherein each cannula of the at least one cannula comprises a harpoon operable to engage the natural fiducial.

19. The method of claim 18, wherein the harpoon comprises:
a self-penetrating tip;
a foreshaft distally coupled to the self-penetrating tip, the foreshaft defining a radial aperture disposed along a longitudinal axis of the foreshaft;
a pushrod, having a proximal end defining an axial socket sized for and releasably coupled to a distal end of the foreshaft;
optionally, a tether looped through the radial aperture; and
optionally, at least one spur, operably coupled to the self-penetrating head, configured to transition from a first insertion position to a second anchoring position.

20. The method of claim 19, wherein the step of engaging the annular target at the location aligned with the at least one natural fiducial comprises:
using the pushrod, penetrating the location aligned with the at least one natural fiducial with the self-penetrating tip, wherein at least a portion of the foreshaft remains external to the location aligned with the at least one natural fiducial; and
optionally, transitioning the at least one spur to the anchoring position.

21. The method of claim 20, wherein each sleeve is sized and configured to accommodate the self-penetrating tip, the foreshaft, and optionally, the at least one spur.

22. The method of claim 21, wherein each sleeve further comprises a dorsal peg extending radially from the sleeve.

23. The method of claim 22, wherein each coupling sub-assembly comprises a docking head coupled to the outer hollow tube, operable to releasably engage the sleeve.

24. The method of claim 23, wherein each coupling sub-assembly further comprises:

a washer, operably coupled to the peg, forming a peg with a flange; and a pair of release cords, wherein the docking head further defines an opening having a cylindrical internal surface, configured to accommodate the peg, with two pairs of diametrically aligned openings defined in the docking head, a distance between each pair sized and configured to be wider than the peg and narrower than the flange, such that the pair of release cords is each threaded through the diametrically opposed openings between the flange and the sleeve.

25. The method of claim 24, wherein the step of releasing the sleeve from the outer hollow tube comprises:

pulling the release cords; and using the delivery catheter, releasing each sleeve from the outer hollow tube.

26. The method of claim 20, wherein the annuloplasty ring or a second toroidal portion thereof has one or more zones, each zone comprising a plurality of internal anchor heads located at least partially within the outer hollow tube, the zones of the annuloplasty ring, or the second toroidal portion thereof disposed opposite the alignment and engagement construction, each internal anchor head of the plurality of internal anchor heads are operable to selectably extend radially from the outer hollow tube and engage a portion of the annular target.

27. The method of claim 26, wherein the at least one natural fiducial is at least one of a right fibrous trigon, a left fibrous trigon, an interleaflet triangle, and a tricuspid posterior-anterior hinge.

28. The method of claim 27, wherein the annular target is at least one of: a mitral valve, a tricuspid valve, an aortic valve, and a pulmonary valve.

29. The method of claim 28, wherein the annular target is the mitral valve, the natural fiducials are the right fibrous trigon and the left fibrous trigon, and wherein the sleeves are radially spaced to align with and engage the right fibrous trigon and the left fibrous trigon, sequentially or simultaneously.

30. The method of claim 29 further comprising:

either simultaneously or sequentially, with releasing the pushrod from the foreshaft;

using the delivery catheter, maneuvering the one or more zones, each comprising the plurality of internal anchor heads of the annuloplasty ring or the second toroidal portion thereof to a posterior rim of the mitral valve;

deploying the plurality of internal anchor heads of the second toroidal portion thereby engaging the posterior rim of the mitral valve; and using the tethers, pulling the posterior rim of the mitral valve toward the natural fiducials.

31. The method of claim 30, wherein the annuloplasty ring or the first toroidal portion thereof has one or more zones, each zone comprising a plurality of internal anchor heads located at least partially within the outer hollow tube, the zones of the annuloplasty ring, or the first toroidal portion thereof, each internal anchor head of the plurality of internal anchor heads are operable to selectably extend radially from the outer hollow tube in line with the alignment and engagement construction, and engage an anterior portion of the mitral valve.

32. The method of claim 31, further comprising:

deploying the plurality of internal anchor heads of the first toroidal portion configured to engage an anterior rim of the mitral valve;

anchoring the anterior rim of the mitral valve to the annuloplasty ring or the first toroidal portion thereof;

pulling release cords, thereby releasing the sleeve from the annuloplasty ring or the first toroidal portion thereof;

using the delivery catheter, retracting each cannula and sleeve; and releasing the annuloplasty ring or the first toroidal portion thereof from the delivery catheter.

33. The method of claim 32, wherein the first toroidal portion and the second toroidal portion are operable to form the annuloplasty ring.

34. The method of claim 19, wherein the self-penetrating tip, the foreshaft and optionally the at least one spur are integrated to a single penetrating head.

35. The method of claim 34, wherein the single penetrating head is operable to transition between an insertion configuration and an anchoring configuration.

36. The method of claim 35, wherein the single penetrating head is comprised of a plurality of lancing members, configured to form a filled cylinder having a conical tip.

37. The method of claim 35, wherein the single penetrating head is comprised of a plurality of lancing members, configured to form a hollow cylinder having a frusto-conical conical tip.

38. The method of claim 36, further comprising:

actuating the single penetrating head; and curving the tip of each lancing member of the plurality of lancing members to direct the tip to a distal end of the single penetrating head.

* * * * *